United States Patent [19]
Romers et al.

[11] Patent Number: 5,902,920
[45] Date of Patent: May 11, 1999

[54] PROCESS FOR THE ISOMERIZATION OF OLEFINS

[75] Inventors: Eric Romers, Limelette; Christian Lamotte, Arquennes, both of Belgium

[73] Assignee: Fina Research, S.A., Feluy, Belgium

[21] Appl. No.: 08/695,452

[22] Filed: Aug. 12, 1996

[30] Foreign Application Priority Data

Aug. 11, 1995 [EP] European Pat. Off. .............. 95112725

[51] Int. Cl.⁶ ...................................................... C07C 5/22
[52] U.S. Cl. ............................................ 585/671; 585/664
[58] Field of Search ...................... 585/671, 664

[56] References Cited

U.S. PATENT DOCUMENTS 4,587,375  5/1986  Debras et al. ........................... 585/671

FOREIGN PATENT DOCUMENTS 0240480  10/1987  European Pat. Off. .......... C07C 2/12

*Primary Examiner*—Glenn Caldarola
*Assistant Examiner*—In Suk Bullock
*Attorney, Agent, or Firm*—Jimmy D. Wheelington; M. Norwood Cheairs

[57] ABSTRACT

Silicalite to be used as catalyst in the isomerization of olefins is pretreated by passing steam thereon at a temperature of 300 to 750° C. Particularly, isobutene is selectively produced by isomerization of n-butenes.

58 Claims, No Drawings

PROCESS FOR THE ISOMERIZATION OF OLEFINS

BACKGROUND OF THE INVENTION

1. Field of the Invention

The present invention relates to the isomerization of olefins. More particularly, it relates to an improvement in a process for the isomerization of olefins over silicalite.

2. Description of Prior Art

U.S. Pat. No. 4,587,375 discloses a process for the isomerization of n-butenes comprising:

providing a feed containing at least 10 vol % n-butenes; and contacting said feed with silicalite at a temperature of at least about 300° C. in the presence of steam in a water/feed molar ratio of about 0.5-5. However that process provides reaction products containing water. Further, that process produces excessive amounts of liquid by-products. Also, it has been observed that deactivation of the silicalite is excessive for the process to be industrially applicable.

There is thus a need in art for an improvement of the existing isomerization processes of olefins over silicalite.

SUMMARY OF INVENTION

The process of the invention comprises the steps of:

passing steam, either pure or diluted in an inert gas, over silicalite at a temperature of from 300 to 750° C.;

providing a feed containing (i) at least 10 vol % of n-butene and (ii) isobutene if any in an isobutene:n-butene ratio of maximum 1:2;

passing said feed over said silicalite at a temperature of at least 500 C.; and recovering a stream containing an increased amount of isobutene.

DETAILED DESCRIPTION OF THE INVENTION

Silicalite as used herein is an unmodified crystalline silica polymorph as was disclosed in U.S. Pat. No. 4,061,724; said patent discloses a method for preparing silicalite. Steam is passed over silicalite at a temperature of from 300 to 750° C., preferably 450 to 600° C., either pure or diluted in an inert gas (inert gas as used herein is a gas that will not react with silicalite at the relevant temperature, such as nitrogen). The dilution factor, if any, may be of 1:99 to 99:1. Silicalite must be treated with steam during at least 24 hours, preferably at least 72 hours. Atmospheric pressure is generally used, but higher or lower pressures can be used. The space velocity is adapted to the duration of that step, and is generally comprised between 1 and 100 ml water per ml silicalite and per hour, preferably around 10 ml/ml.h. All space velocities herein are space velocities wherein the volumes are measured at normal temperature and pressure.

The feed must contain at least 10 vol % of n-butenes, and isobutene if any in an isobutene:n-butene ratio of maximum 1:2 (preferably <1:5, most preferably <1:10); other hydrocarbons are the main other constituents. Preferably, the feed is an isobutene-depleted mixture of $C_4$ hydrocarbons, as is e.g. recovered from a methyl t-butyl ether (MTBE) unit. Other feeds can be FCC offgases and thermal cracking offgases.

The feed is passed over silicalite at a temperature of at least 500° C., preferably from 500 to 650° C. That step is carried out in the gaseous phase, preferably at about atmosphere pressure. Space velocities can range from 0.05 to 50 $h^{-1}$, preferably from 0.5 to 30 $h^{-1}$.

It is particularly advantageous to separate unreacted hydrocarbons present in the effluent from the isobutene present in said effluent and then to recycle the unreacted hydrocarbons back into the feed.

The silicalite is generally shaped by extrusion. It is generally also composited (preferably during said extrusion) with inorganic matrix materials (often named binders), because it tends to be subject to physical collapse and attrition during normal loading and unloading of the reaction zone as well as during the process. Where a matrix material is used, it is highly preferred that the matrix be substantially free of hydrocarbon conversion actively; most preferred are extruded silica polymorph silicalite catalysts consisting essentially of silicalite. Suitable matrix materials can be selected from alumina, silica, zirconia, silicamagnesia and clays; alumina is generally preferred.

The steam treatment can be carried out either before extrusion, preferably on the silicalite as such, or after extrusion.

The run life of the silicate can be increased by periodically stopping the flow of feed and stripping the silicalite with a gas selected from inert gases, oxidizing gases and mixtures thereof, preferably air, at a temperature of 300 to 750° C., preferably 450 to 675° C., most preferably about 600° C. Inert gas as used herein is a gas that will not react with silicalite itself at the relevant temperature, such as nitrogen; oxidizing gas as used herein is a gas such as oxygen that will react at the relevant temperature with carbonaceous deposits on the silicalite to form carbon oxides. Stripping is carried out at a pressure from atmospheric to 1 MPa, preferably from above atmospheric to 0.5 MPa, most preferably of about 0.3 MPa. It is continued until the outlet gas composition is substantially equal to the inlet gas composition; when an oxidizing gas is used, it is convenient to monitor carbon dioxide concentration in the outlet gas. The performances after regeneration are substantially identical to those observed initially.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

An isobutene-depleted mixture of $C_4$ hydrocarbons was recovered from a MTBE unit; it had the following composition (wt %):

$C_3$ hydrocarbons 0.2
n-butane 12.0
isobutane 31.2
1-butene 22.0
cis-2-butene 11.9
trans-2-butene 18.4
isobutene 3.2
$C_5$ and heavier 1.1

A commercial catalyst was obtained, which had the following characteristics:

(a) silicalite 80 wt %
$SiO_2/Al_2O_3$ molar ratio 240
crystal size 0.001–0.01 mm
surface area 357 $m^2/g$ delta d at 28° (2 theta) 0.0035 nm (Co K alpha X-ray diffraction)

crystal structure monoclinic $Na_2O$<500 ppmw $K_2O$<500 ppmw (b) $Al_2O_3$ binder 20 wt %

15 ml catalyst were steamed under the following conditions:

flow of 90 l nitrogen and 190 ml water per hour;

temperature rising from 25 to 550° C. at 52.5° C./h, then of 550° C. during 96 hours;

atmospheric pressure.

10 ml of steamed catalyst were introduced in a reactor and preconditioned during 10 hours at 550° C. by passing thereover 20 Nl/h of air under atmospheric pressure.

The feed was then passed over the catalyst using the following operating conditions:

atmospheric pressure

550° C. (isothermal reactor)

LHSV=25 l/l.h downflow mode

After 12 days, the feed flow was interrupted to strip the catalyst with 30 Nl air per hour at 580° C. under 0.3 MPa gauge pressure until $CO_2$ concentration at the outlet was below 100 ppm.

The feed was then passed over the regenerated catalyst under the same conditions as previously.

The results are indicated in Table 1. Conversion and yield are calculated as follows:

$$\text{conversion \%} = \frac{(1\text{-butene} + 2\text{-butenes})_{in} - (1\text{-butene} + 2\text{-butenes})_{out}}{(1\text{-butene} + 2\text{-butenes})_{in}} \times 100$$

$$\text{yield \%} = \frac{(\text{isobutylene})_{out} - (\text{isobutylene})_{in}}{(1\text{-butene} + 2\text{-butenes})_{in}} \times 100$$

In Table 2, yields have been calculated for various hydrocarbons in the first run, using the hereabove formula mutatis mutandis.

TABLE 1 results obtained in example 1 and comparative example A

| | Example 1 | | Comparative example A | |
|---|---|---|---|---|
| day | conversion % | yield % | conversion % | yield % |
| 1 | 49 | 21.7 | 86 | 5.1 |
| 2 | 54 | 18.3 | 84 | 7.3 |
| 3 | 55 | 21.1 | 80 | 10.2 |
| 4 | 56 | 20.9 | 74 | 14.5 |
| 5 | 57 | 20.6 | 61 | 19.8 |
| 6 | 57 | 20.5 | 43 | 17.5 |
| 7 | 57 | 20.5 | 20 | 10.0 |
| 8 | 56 | 20.6 | (stopped) | |
| 9 | 56 | 20.7 | | |
| 10 | 55 | 19.0 | | |
| 11 | 51 | 20.9 | | |
| 12 | 49 | 21.4 | | |
| 13 | 42 | 20.4 | | |
| 14 | 49 | 20.9 | | |
| 15 | 53 | 20.3 | | |
| 16 | 54 | 20.2 | | |
| 17 | 54 | 19.4 | | |
| 18 | 54 | 19.2 | | |
| 19 | 54 | 20.5 | | |
| 20 | 53 | 19.1 | | |

TABLE 1-continued results obtained in example 1 and comparative example A

| | Example 1 | | Comparative example A | |
|---|---|---|---|---|
| day | conversion % | yield % | conversion % | yield % |
| 21 | 49 | 20.5 | | |
| 22 | 49 | 19.7 | | |
| 23 | 47 | 19.9 | | |
| 24 | 46 | 20.9 | | |
| | (stopped) | | | |

TABLE 2 yield % for various hydrocarbons in run 1

| | Example 1 | Comp. ex. A | Example 2 | Comp. ex. B |
|---|---|---|---|---|
| methane | +0.1 | +1.0 | +0.1 | +0.8 |
| ethane | 0.0 | +0.9 | 0.0 | +0.9 |
| ethylene | +0.8 | +13.3 | +0.5 | +15.4 |
| propane | +0.1 | +6.5 | +0.3 | +6.2 |
| propylene | +11.6 | +28.8 | +7.5 | +35.6 |
| butanes | +1.5 | 0.0 | 0.0 | +0.3 |
| isobutene | +21.7 | +5.1 | +22.8 | +2.4 |
| pentanes | 0.0 | +3.7 | 0.0 | +1.7 |
| pentenes | +11.2 | +4.7 | +7.9 | +7.0 |
| C > 5 | +2.0 | +22.0 | +1.0 | +14.8 |

Comparative Example A

Example 1 was repeated, except that the catalyst steaming step was omitted. The results are also indicated in Tables 1 and 2.

As can readily be seen, the prior steaming of the catalyst has the unexpected effects of dramatically increasing its useful life (Table 1) and the isobutene selectivity (Table 2) as well as reducing the amount of liquid by-products (C>5).

EXAMPLE 2

Example 1 was repeated with a commercial silicalite catalyst without binder. The commercial silicalite, as obtained, had the following properties:

$SiO_2/Al_2O_3$ molar ratio 240 crystal size 0.001–0.01 mm surface area 399 $m^2/g$ delta d at 28° (2 theta) 0.0035 nm (Co K alpha X-ray diffraction)

crystal structure monoclinic $Na_2O$ <500 ppmw $K_2O$<500 ppmw

The results are indicated in Table 3. Conversion and yield are calculated as for example 1. In Table 2, yields have been calculated for various hydrocarbons in the first run, as has been done for example 1.

TABLE 3 results obtained in example 2 and comparative example B

| | Example 2 | | Comparative example B | |
|---|---|---|---|---|
| day | conversion % | yield % | conversion % | yield % |
| 1 | 40.0 | 20.2 | 85.1 | 2.4 |
| 2 | 39.9 | 19.6 | 84.6 | 2.9 |
| 3 | 37.3 | 19.0 | 83.8 | 3.5 |
| 4 | 35.7 | 18.4 | 82.0 | 4.3 |
| 5 | 33.7 | 17.9 | 79.9 | 5.7 |
| 6 | 35.2 | 17.2 | 74.3 | 9.6 |
| 7 | 30.6 | 16.2 | 67.6 | 14.2 |
| 8 | 29.3 | 15.0 | 55.9 | 19.1 |
| 9 | 23.5 | 15.2 | 32.9 | 16.2 |
| 10 | 21.7 | 13.8 | 17.7 | 9.5 |
| 11 | 19.0 | 12.8 | 10.5 | 4.7 |
| 12 | 24.3 | 16.2 | 7.3 | 2.4 |
| | (stopped) | | (stopped) | |

Comparative Example B

Example 2 was repeated, except that the silicalite steaming step was omitted. The results are also indicated in Tables 2 and 3.

As can readily be seen, the prior steaming of the silicalite catalyst without binder has the effect of dramatically increasing the useful life of the catalyst (Table 3) and the isobutene yield (Table 2). It has to be noticed that the yield to liquid hydrocarbons (C>5) is reduced drastically.

EXAMPLE 3

Example 2 was repeated with a commercial silicalite catalyst without binder. An isobutene-depleted mixture of C4 hydrocarbons was recovered from a MTBE unit; it had the following composition (wt %).

C3 hydrocarbons 0.2 n-butane 11.3 isobutane 35.7

1-butene 19.2 cis-2-butene 12.2 trans-2-butene 17.7 isobutene 1.8

C5 and heavier 1.5

A commercial catalyst was obtained, which had the following characteristics:

$SiO_2/Al_2O_3$ molar ratio 50.4 crystal size 0.001–0.01 mm surface area 441 m$^2$/g delta d at 28° – crystal structure <60% monoclinic $Na_2O$ <500 ppmw $K_2O$ <500 ppmw

The results are indicated in Table 4; Conversion and yield are calculated as for example 1. In table 5, yields have been calculated for various hydrocarbons in the first run, as has been done for example 1.

TABLE 4 results in example 3 and comparative example C

| | Example 3 | | Comparative example C | |
|---|---|---|---|---|
| day | conversion % | yield % | conversion % | yield % |
| 1 | 51 | 17.6 | 93 | 1.1 |
| 2 | 50 | 18.2 | 86 | 5.5 |
| 3 | 46 | 17.5 | 73 | 13.7 |
| 4 | 44 | 17.2 | 36 | 19.7 |
| 5 | 41 | 16.7 | 8 | 4.6 |
| 6 | 42 | 17.6 | 3 | 1.0 |
| 7 | 43 | 16.1 | stopped) | |
| 8 | 43 | 16.1 | | |
| 9 | 38 | 16.3 | | |
| 10 | 40 | 16.3 | | |
| 11 | 33 | 14.9 | | |
| 12 | 29 | 13.2 | | |
| | (stopped) | | | |

TABLE 5 yield % for various hydrocarbons in example 3 and comparative example C for run 1

| | Example 3 | Comparative example C |
|---|---|---|
| methane | +0.0 | 4.6 |
| ethane | +0.0 | 4.5 |
| ethylene | +1.1 | 13.9 |
| propane | +0.2 | 29.8 |
| propylene | +14.3 | 21.0 |
| butanes | +1.6 | 0.0 |
| isobutene | +17.6 | 1.1 |
| pentanes | +1.1 | 2.0 |
| pentenes | +10.6 | 1.2 |
| C > 5 | +4.0 | 14.7 |

Comparative example C

Example 3 was repeated, except that the silicalite steaming step was omitted. The results are also indicated in Tables 4 and 5.

EXAMPLE 4

Example 2 was repeated with a prepared silicalite catalyst without binder. The separation is based on U.S. Pat. No. 4,061,724. An isobutene-depleted mixture of C4 hydrocarbons was recovered from a MTBE unit; it had the following composition (wt %).

C3 hydrocarbons 0.1 n-butane 12.4 isobutane 19.3

1-butene 36.5 cis-2-butene 7.7 trans-2-butene 15.8 isobutene 1.2

C5 and heavier 7.1

The catalyst was obtained after preparation and had the following characteristics:

$SiO_2/Al_2O_3$ molar ratio 892 crystal size 0.001–0.01 mm surface area 394 m$^2$/g delta d at 28° – crystal structure ..% monoclinic
Na₂O <500 ppmw
K₂O <500 ppmw

The results are indicated in Table 6; Conversion and yield are calculated as for example 1. In table 7, yields have been calculated for various hydrocarbons in the first run, as has been done for example 1.

TABLE 6 results in example 4 and comparative example D

| | Example 3 | | Comparative example D | |
|---|---|---|---|---|
| day | conversion % | yield % | conversion % | yield % |
| 1 | 64 | 18.0 | 82 | 9.7 |
| 2 | 62 | 17.8 | 80 | 10.7 |
| 3 | 53 | 22.1 | 77 | 3.3 |
| 4 | 55 | 20.8 | 75 | 14.6 |
| 5 | 52 | 22.5 | 72 | 16.3 |
| 6 | 50 | 23.3 | 70 | 17.9 |
| 7 | 49 | 23.5 | 67 | 18.4 |
| 8 | 48 | 24.0 | 61 | 21.8 |
| 9 | 48 | 23.3 | 56 | 23.1 |
| 10 | 48 | 20.8 | 58 | 21.3 |
| 11 | 47 | 22.8 | 59 | 19.9 |
| 12 | 49 | 19.2 | 47 | 17.4 |
| 13 | 43 | 20.5 | 41 | 11.2 |
| | (stopped) | | (stopped) | |

TABLE 7 yield % for various hydrocarbons in example 4 and comparative example D for run 1

| | Example 4 | Comparative example D |
|---|---|---|
| methane | +0.2 | 0.9 |
| ethane | +0.0 | 0.3 |
| ethylene | +2.3 | 9.3 |
| propane | +0.3 | 1.8 |
| propylene | +21.6 | 33.6 |
| butanes | +4.5 | 4.6 |
| isobutene | +18.0 | 9.7 |
| pentanes | +0.0 | 2.1 |
| pentenes | +15.4 | 9.0 |
| C > 5 | +1.7 | 10.7 |

Comparative example D

Example 4 was repeated, except that the silicalite steaming step was omitted. The results are also indicated in Tables 6 and 7.

The examples 2 to 4 show that the steaming stabilizes the butenes conversion and the iso-butene production. Whilst not wishing to be bound by a theory, it is believed that after steaming the pores are blocked by the dealumination of the silicalite, which stabilizes the iso-butene yield.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. Process for the isomerization of olefins, comprising the steps of:
   a) passing steam, either pure or diluted in an inert gas, over silicalite at a temperature of from 300 to 750° C.;
   b) providing a feed containing (i) at least 10 vol % of n-butene and (ii) isobutene if any in an isobutene:n-butene ratio of maximum 1:2;
   c) passing said feed over said silicalite at a temperature of at least 500° C.; and
   d) recovering a stream containing an increased amount of isobutene.

2. Process according to claim 1, wherein steam is passed over silicalite at a temperature of 450 to 600° C.

3. Process according to claim 1, wherein steam is diluted in an inert gas in a ratio of 1:99 to 99:1.

4. Process according to claim 2, wherein steam is diluted in an inert gas in a ratio of 1:99 to 99:1.

5. Process according to claim 1, wherein steam is passed over silicalite during at least 24 hours.

6. Process according to claim 2, wherein steam is passed over silicalite during at least 24 hours.

7. Process according to claim 3, wherein steam is passed over silicalite during at least 24 hours.

8. Process according to claim 1, wherein steam is passed over silicalite at a space velocity comprised between 1 to 100 ml water per ml silicalite and per hour.

9. Process according to claim 2, wherein steam is passed over silicalite at a space velocity comprised between 1 to 100 ml water per ml silicalite and per hour.

10. Process according to claim 3, wherein steam is passed over silicalite at a space velocity comprised between 1 to 100 ml water per ml silicalite and per hour.

11. Process according to claim 4, wherein steam is passed over silicalite at a space velocity comprised between 1 to 100 ml water per ml silicalite and per hour.

12. Process according to claim 1, comprising the additional steps of separating unreacted hydrocarbons present in the effluent from the isobutene present therein, and recycling the unreacted hydrocarbons back into the feed.

13. Process according to claim 2, comprising the additional steps of separating unreacted hydrocarbons present in the effluent from the isobutene present therein, and recycling the unreacted hydrocarbons back into the feed.

14. Process according to claim 3, comprising the additional steps of separating unreacted hydrocarbons present in the effluent from the isobutene present therein, and recycling the unreacted hydrocarbons back into the feed.

15. Process according to claim 4, comprising the additional steps of separating unreacted hydrocarbons present in the effluent from the isobutene present therein, and recycling the unreacted hydrocarbons back into the feed.

16. Process according to claim 5, comprising the additional steps of separating unreacted hydrocarbons present in the effluent from the isobutene present therein, and recycling the unreacted hydrocarbons back into the feed.

17. Process according to claim 1, wherein an extruded polymorph silicalite catalyst consisting essentially of silicalite is used.

18. Process according to claim 2, wherein an extruded polymorph silicalite catalyst consisting essentially of silicalite is used.

19. Process according to claim 3, wherein an extruded polymorph silicalite catalyst consisting essentially of silicalite is used.

20. Process according to claim 4, wherein an extruded polymorph silicalite catalyst consisting essentially of silicalite is used.

21. Process according to claim 5, wherein an extruded polymorph silicalite catalyst consisting essentially of silicalite is used.

22. Process according to claim 6, wherein an extruded polymorph silicalite catalyst consisting essentially of silicalite is used.

23. Process according to claim 17, wherein the steam is passed over the silicalite before extrusion.

24. Process according to claim 18, wherein the steam is passed over the silicalite before extrusion.

25. Process according to claim 19, wherein the steam is passed over the silicalite before extrusion.

26. Process according the claim 20, wherein the steam is passed over the silicalite before extrusion.

27. Process according the claim 21, wherein the steam is passed over the silicalite before extrusion.

28. Process according the claim 22, wherein the steam is passed over the silicalite before extrusion.

29. Process according to claim 1, when used for the selective isomerization of n-butenes into isobutylene.

30. Process according to claim 2, when used for the selective isomerization of n-butenes into isobutylene.

31. Process according to claim 3, when used for the selective isomerization of n-butenes into isobutylene.

32. Process according to claim 4, when used for the selective isomerization of n-butene into isobutylene.

33. Process according to claim 5, when used for the selective isomerization of n-butenes into isobutylene.

34. Process according to claim 6, when used for the selective isomerization of n-butenes into isobutylene.

35. Process according to claim 7, when used for the selective isomerization of n-butenes into isobutylene.

36. Process according to claim 8, when used for the selective isomerization of n-butenes into isobutylene.

37. Process according to claim 9, when used for the selective isomerization of n-butenes into isobutylene.

38. Process according to claim 10, when used for the selective isomerization of n-butenes into isobutylene.

39. Process according to claim 11, when used for the selective isomerization of n-butenes into isobutylene.

40. Process according to claim 12, when used for the selective isomerization of n-butenes into isobutylene.

41. Process according to claim 13, when used for the selective isomerization of n-butenes into isobutylene.

42. Process according to claim 14, when used for the selective isomerization of n-butenes into isobutylene.

43. Process according to claim 15, when used for the selective isomerization of n-butenes into isobutylene.

44. Process according to claim 16, when used for the selective isomerization of n-butenes into isobutylene.

45. Process according to claim 17, when used for the selective isomerization of n-butenes into isobutylene.

46. Process according to claim 18, when used for the selective isomerization of n-butenes into isobutylene.

47. Process according to claim 19, when used for the selective isomerization of n-butenes into isobutylene.

48. Process according to claim 20, when used for the selective isomerization of n-butenes into isobutylene.

49. Process according to claim 21, when used for the selective isomerization of n-butenes into isobutylene.

50. Process according to claim 22, when used for the selective isomerization of n-butenes into isobutylene.

51. Process according to claim 23, when used for the selective isomerization of n-butenes into isobutylene.

52. Process according to claim 5, wherein steam is passed over silicalite during at least 72 hours.

53. Process according to claim 6, wherein steam is passed over silicalite during at least 72 hours.

54. Process according to claim 7, wherein steam is passed over silicalite during at least 72 hours.

55. Process according to claim 8, wherein steam is passed over silicalite at a space velocity comprised around 10 ml water per ml silicalite and per hour.

56. Process according to claim 9, wherein steam is passed over silicalite at a space velocity comprised around 10 ml water per ml silicalite and per hour.

57. Process according to claim 10, wherein steam is passed over silicalite at a space velocity comprised around 10 ml water per ml silicalite and per hour.

58. Process according to claim 11, wherein steam is passed over silicalite at a space velocity comprised around 10 ml water per ml silicalite and per hour.

* * * * *